US006593496B1

(12) United States Patent  
Quallich

(10) Patent No.: US 6,593,496 B1  
(45) Date of Patent: Jul. 15, 2003

(54) PROCESS FOR PREPARING SERTRALINE FROM CHIRAL TETRALONE

(75) Inventor: George H. Quallich, Groton, CT (US)

(73) Assignee: Pfizer Inc, New York, NY (US)

( * ) Notice: Subject to any disclaimer, the term of this patent is extended or adjusted under 35 U.S.C. 154(b) by 198 days.

(21) Appl. No.: 09/584,009

(22) Filed: May 30, 2000

Related U.S. Application Data

(60) Provisional application No. 60/138,340, filed on Jun. 9, 1999.

(51) Int. Cl.[7] ................................................ C07C 87/64
(52) U.S. Cl. ........................ 564/270; 564/305; 564/308
(58) Field of Search ................................ 564/270, 305, 564/308

(56) References Cited

U.S. PATENT DOCUMENTS 4,536,518 A    8/1985   Welch, Jr.
4,855,500 A    8/1989   Spavins

FOREIGN PATENT DOCUMENTS

| EP | 0341015 | 8/1989 |
|----|---------|--------|
| WO | 9957095 | 5/1998 |

OTHER PUBLICATIONS

A. Streitweiser and C.H. Heathcock, J. "Introduction to Organic Chemistry" MacMillan Pub. Co. Inc., New York, pp. 124 & 143, 1981.

Willard M. Welch et al., Nontricyclic Antidepressant Agents Derived from cis–and trans–1–Amino–4–aryltetralins, J. Med. Chem. 1984, 27, 1508–1515.

*Primary Examiner*—Samuel Barts
(74) *Attorney, Agent, or Firm*—Peter C. Richardson; Paul H. Ginsburg; A. David Joran

(57) ABSTRACT

This invention relates to a novel improved process for preparing the (+) enantiomer of N-[4(3,4-dichlorophenyl)-3,4-dihydro-1(2H)-naphthalenylidene]methanamine by reacting the (+) enantiomer of 4-(3,4-dichlorophenyl)-3,4-dihydro-1(2H)-naphthalenone with monomethylamine and titanium chloride or molecular sieves.

9 Claims, No Drawings

PROCESS FOR PREPARING SERTRALINE FROM CHIRAL TETRALONE

This application claims the benefit for U.S. Provisional Application No. 60/138,340, filed Jun. 9, 1999.

BACKGROUND OF THE INVENTION

This invention relates to a new, simplified method of preparing a known ketimine compound. Specifically, it is concerned with the synthesis of the (+) enantiomer of N-[4-(3,4-dichlorophenyl)-3,4-dihydro-1(2H)-naphthalenylidene]methanamine, a critical intermediate in the production of cis-(1S)(4S)-N-methyl-4(3,4-dichlorophenyl)-1,2,3,4-tetrahydro-1-naphthaleneamine (sertraline). Sertraline hydrochloride is the active ingredient in the antidepressant Zoloft®.

The most widely used route to date for the commercial preparation of N-[4-(3,4-dichlorophenyl)-3,4-dihydro-1(2H)-naphthalenylidene]methanamine, leading to cis-(1S)(4S)-N-methyl-4(3,4-dichlorophenyl)-1,2,3,4-tetrahydro-1-naphthaleneamine (sertraline), involves a condensation reaction of 4-(3,4-dichlorophenyl)-3,4-dihydro-1(2H)-naphthalenone with monomethylamine, which is catalyzed by titanium tetrachloride, as described by W. R. Welch, Jr. et al. in U.S. Pat. No. 4,536,518 and in Journal of Medicinal Chemistry, Vol. 27, No. 11, p 1508, 1984. An alternative method of producing N-[4-(3,4-dichlorophenyl)-3,4-dihydro-1(2H)naphthalenylidene]methanamine is described in U.S. Pat. No. 4,855,500 to J. C. Spavins, wherein the dehydration characteristics of appropriate mesh molecular sieves are employed to promote the condensation reaction between 4-(3,4-dichlorophenyl)-3,4-dihydro-1(2H)naphthalenone and monomethylamine. The appropriate type molecular sieves (specifically, those having a pore size of about 3 Angstroms) are contacted in situ with the mixture of 4-(3,4dichlorophenyl)-3,4-dihydro-1(2H)-naphthalenone and monomethylamine, and adsorb the water formed from the condensation reaction.

Substantial economies can be realized by carrying out similar processes to those described in the preceding paragraph, using the optically pure (+) enantiomer of the tetralone starting material, or an optically enriched (+) mixture of the (+) and (−) enantiomers of the same, rather than racemic tetralone. Use of the chiral starting material eliminates the need to resolve the final product and also eliminates the production of intermediates having the undesired sterochemistry.

SUMMARY OF THE INVENTION

This invention relates to a process for preparing the optically pure (+) enantiomer of N-[4(3,4-dichlorophenyl)-3,4-dihydro-1(2H)-naphthalenylidene]methaneamine, depicted below,

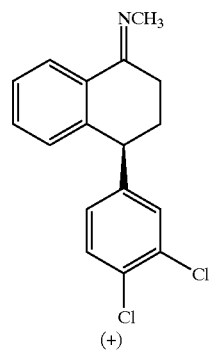

or an optically enriched (+) mixture of the above compound of formula II and its opposite enantiomer, comprising reacting the optically pure (+) enantiomer of 4-(3,4-dichlorophenyl)-3,4dihydro-1(2H)-napthalenone ("the tetralone"), depicted below,

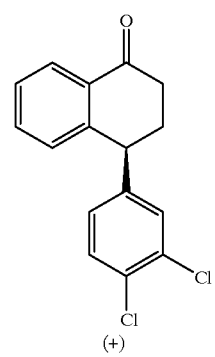

or an optically enriched (+) mixture of the (+) and (−) enantiomers of the tetralone, with monomethylamine and either titanium tetrachloride or molecular sieves in a solvent selected from tetrahydrofuran ("THF"), methylene chloride and aromatic solvents such as toluene, xylenes and dichlorobenzene, at a temperature from about −20° C. to about 60° C., preferably from about 0° C. to about 50° C.

A more specific embodiment of this invention relates to the process described above, wherein: (a) the ketimine product of formula II that is formed in such process is hydrogenated to form a mixture of cis (+) sertraline ("sertraline") and trans (−) sertraline; (b) sertraline is optionally separated from such mixture; and (c) sertraline is optionally converted into its hydrochloride or mandelate salt.

The terms "sertraline" and "cis (+) sertraline", as used herein, both refer to cis-(1S)(4S)-N-methyl-4-(3,4-dichlorophenyl)-1,2,3,4-tetrahydro-1-naphthaleneamine.

The term "trans (+) sertraline", as used herein, refers to trans-(1R) (4S)-N-methyl4-(3,4dichlorophenyl)-1,2,3,4-tetrahydro-1-naphthaleneamine.

The term "cis (−) sertraline", as used herein, refers to cis-(1R) (4R)-N-methyl-4-(3,4dichlorophenyl)-1,2,3,4-naphthaleneamine.

The term "trans (−) sertraline", as used herein, refers to trans-(1S) (4R)-N-methyl4-(3,4dichlorophenyl)-1,2,3,4-naphthaleneamine.

The term "racemic cis sertraline", as used herein, refers to an optically inactive mixture of cis (+) sertraline and cis (−) sertraline.

The term "racemic trans sertraline", as used herein, refers to an optically inactive mixture of trans (+) sertraline and trans (−) sertraline.

The term "racemic sertraline", as used herein, refers to an optically inactive mixture of racemic cis sertraline and racemic trans sertraline.

DETAILED DESCRIPTION OF THE INVENTION

The processes of this invention, as well as the use of the ketimine product of such processes in the synthesis of sertraline, are illustrated in the following schemes and described below.

In accordance with the process of this invention, the starting material, optically pure (+) 4(3,4-dichlorophenyl)-3,4-dihydro-1(2H)-naphthalenone, or an optically enriched (+) mixture of the (+) and (−) enantiomers of the same compound, is combined with 1.5 to 25 equivalents of monomethylamine and a solvent selected from methylene chloride, THF and aromatic solvents such as toluene, zylenes or dichlorobenzene. Titanium tetrachloride (0.2 to 1.2 equivalents) or molecular sieves is combined with the reaction mixture and reacted at a temperature from about −20° C. to about 60° C., preferably from about 0° C. to about 50° C., for about 1 to about 24 hours. Solid by-products (titanium dioxide and monomethylamine hydrochloride) can be removed from the reaction mixture by filtration and washed with the reaction solvent. A suitable filter aid may be utilized to aid filtration. Decolorizing carbon or a suitable filter aid may be added to the solvent containing product, the resulting mixture stirred and filtered off, and the cake washed with the same solvent.

SCHEME 1

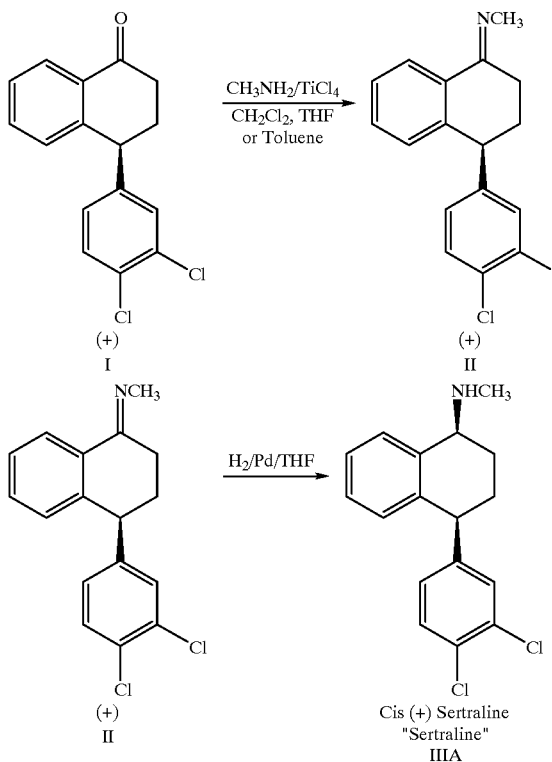

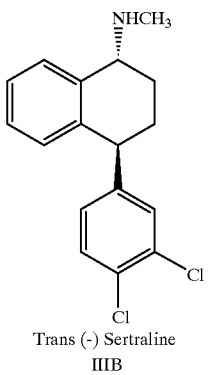

Trans (−) Sertraline
IIIB

SCHEME 2

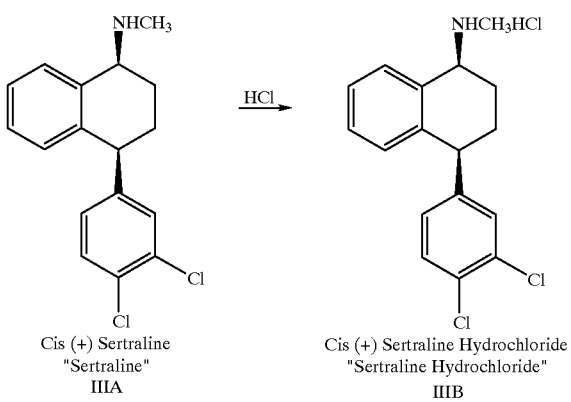

Cis (+) Sertraline
"Sertraline"
IIIA

Cis (+) Sertraline Hydrochloride
"Sertraline Hydrochloride"
IIIB

The solvent containing the (+) ketimine product of formula II, or an optically enriched (+) mixture of the (+) and (−) enantiomers of the same, can then be concentrated by distillation (either atmospherically or under reduced pressure) and then essentially displaced by hexane to a final volume of 3–10 liters per kilogram of starting material. The ketimine product is granulated at a temperature from about at −10° C. to about 30° C., filtered and washed with hexanes or heptane. Such product can be used directly, solvent wet, in the next step (i.e., the hydrogenation step), or, if needed for storage, it can be dried under vacuum or atmospherically at a maximum temperature of 80° C.

If THF is used as the reaction solvent for the ketimine formation reaction, the solvent containing the ketimine product can be concentrated by distillation (either atmospherically or under reduced pressure) and the concentrated solution carried directly into the next step. The dried or solvent wet ketimine product from the above step is combined with THF. The solution is hydrogenated in suitable equipment using up to 30% (weight/weight) of a hydrogenation catalyst such as palladium on carbon water wet catalyst or palladium on calcium carbonate water wet catalyst, or one of the analogous platinum containing catalysts, to produce a mixture of cis (+) sertraline and trans (−) sertraline. The hydrogen pressure for the hydrogenation reaction is from about 1 to about 8 atmospheres, preferably from about 1 to about 5 atmospheres, and the temperature is from about 0° to about 70° C., preferably from about room temperature to about 60° C. The reaction time is generally from about 1 to about 24 hours. The catalyst is then filtered off and washed with the same solvent used for the hydrogenation reaction, and the filtrate is further processed as described below.

If toluene is used as the solvent for the ketimine formation reaction, the solvent containing the ketimine product can be concentrated by distillation (either atmospherically or under reduced pressure) and then hydrogenated, as described above, but using toluene as the hydrogenation solvent, to produce a mixture of cis (+) sertraline and trans (−) sertraline.

The hydrogenation reaction can also be conducted in other solvents such as ethanol, isopropyl ether, methyl t-butyl ether and like solvents, although, depending on the solvent used for the ketimine formation reaction, it may be preferable to isolate the dried ketimine prior to combining it with the hydrogenation solvent. Following completion of the hydrogenation reaction, a filtration is performed to remove the catalyst. Excess monomethylamine is removed via distillation and/or displacement of the original solvent (used for the ketimine formation reaction reaction) with another suitable solvent such as a lower alkanol, tetrahydrofuran, methyl ethyl ketone, or toluene.

The preferred temperature range for the hydrogenation reaction is from about 0° C. to about 70° C., and the preferred range of hydrogen pressures is from about 1 atmosphere to about 8 atmospheres. The most preferable temperatures are within the range of about room temperature to about 60° C., and the most preferable hydrogen pressures are within the range of about 1 atmospheres to about 5 atmospheres.

Preferable catalysts for the reduction or reductive amination described above include platinum, palladium and other precious metal promoters on supports such as carbon, graphite, calcium carbonate or other such supports, all of which are well known in the catalytic hydrogenation industry.

The hydrochloride salt of sertraline can be obtained as follows. Hydrogen chloride, either as a gas or an aqueous solution, is combined with the filtrate from the hydrogenation reaction and the resulting product is selectively crystallized to isolate cis (+) sertraline ("sertraline"), granulated at a temperature from about −10° C. to 30° C., filtered and washed with the reaction solvent. The resulting sertraline hydrochloride salt can be used directly, solvent wet, in further processing, or, if needed for storage, dried at less than 80° C., either atmospherically or under reduced pressure.

When toluene is used as the hydrogenation solvent, the sertraline mandelate salt can be formed by combining the filtrate from the hydrogenation reaction with 0.9 to 1.5 equivalents of D-(−)-mandelic acid, at a temperature from about 0° C. to about 80° C., either directly or as a slurry/solution in ethanol. The resulting product is the sertraline mandelate salt (i.e., the cis (+) sertraline mandelate salt), with only trace amounts of the trans (−) sertraline mandelate. This is because D-(−)-mandelic acid converts both trans-(−)-sertraline and cis (−) sertaline into cis (+) sertraline mandelate ("sertraline mandelate"). The resulting product is then granulated at a temperature from about −10° C. to about 30° C., filtered and washed with ethanol. The sertraline mandelate so obtained can then be used directly, solvent wet, in further processing or dried at less than 80° C., either atmospherically or under reduced pressure.

The above reaction with D-(−)-mandelic acid can also be carried out in a variety of other solvents (e.g., THF, ethanol, methanol, isopropanol, ethyl acetate, acetone, isopropyl ether, or methyl t-butyl ether), although, depending on the hydrogenation solvent used, it may be preferable to isolate the sertraline free base after the hydrogenation reaction.

As an alternative to concentrating and isolating the solid ketimine product from the ketimine formation reaction, the solvent/ketimine mixture from that reaction can be processed directly forward, without isolation, to the next synthetic step in the production of sertraline, whereby catalytic hydrogenation of the ketimine to form a mixture of cis (+) and trans (−) sertraline is performed using the same solvent. The hydrogenation can be carried out successfully, either after the ketimine formation is complete, or concurrently with the ketimine formation, in a reductive amination manner. The reductive animation approach involves combining the (+) tetralone with monomethylamine (ideally 2.5 to 3.5 mole equivalents) and a suitable hydrogenation catalyst, such as those referred to above, under a hydrogen atmosphere, in a suitable organic solvent such as toluene or THF, until hydrogen uptake ceases or the reaction is otherwise shown to be complete. This reaction is typically carried out at a temperature from about 20° C. to about 100° C., preferably from about room temperature to about 70° C., at a pressure from about 20 psig to about 100 psig, preferably from about 20 psig to about 60 psig. Under these conditions, the (+) tetralone is converted into the corresponding (+) ketimine and immediately reduced to the desired mixture of cis (+) sertraline and trans (−) sertraline.

The following examples illustrate, but do not limit in scope, the novel processes of this invention.

EXAMPLE 1

(+) ENANTIOMER OF N-[4-(3,4-DICHLOROPHENYL)-3,4-DIHYDRO-1(2H)-NAPTHALENYLIDENE]METHANEAMINE

To 18.0 g of compound I in 18.5 mL of toluene at −10° C. under nitrogen was added 8.64 g (4.5 equivalents) monomethylamine and the mixture was stirred for 10 minutes. Titanuim tetrachloride (4.57 g, 0.56 equivalents) was added dropwise, keeping the temperature below 15° C. The reaction mixture was allowed to warm to ambient temperature and then stirred for 1 ½ hours. The reaction mixture was filtered under nitrogen, the cake was washed with toluene, and most of the toluene was removed by distillation under vacuum. When approximately 90 mL toluene remained, the vacuum was broken and 72 mL hexane was added. This process was continued until all the toluene was removed, with hexane being added as needed. After distillation was complete, the product was left overnight in the refrigerator and then granulated in 72 mL hexane for 2 hours at 0° C. The resulting mixture was filtered and washed with cold hexane. A light yellow solid was obtained, having a wet weight (wt) of 15.59 g. The product was dried over the weekend in a vacuum oven, after which 14.96 g of product was obtained. The filtrate was stripped off, 20 mL hexane was added and the mixture was left in the refrigerator over the weekend. It was then stirred for 1 hour at 0° C., filtered and washed with cold hexane. The wet weight of the resulting solid product was 1.54 g. The product was dried under vacuum overnight, giving 1.53 g (88%) of a yellow solid.

NMR matched that of the title compound.

EXAMPLE 2

SERTRALINE MANDELATE

To Pd/C (0.740 g, 50% water wet) was added 14.8g of compound II and 65 mL THF under nitrogen. The mixture was hydrogenated at 40 psi for 5 hours. When the reaction was complete, the mixture was filtered through celite and the catalyst cake washed with THF. The solvent was stripped off. Ethanol (EtOH) (74 mL) was added to the residue and the solvent was stripped off. EtOH (74 mL) and D-mandelic acid (7.40 g) were added to the resulting product and the mixture was stirred for 18 hours at ambient temperature. EtOH (14 mL) was then added and the mixture was stirred for 1 hour. The resulting mixture was filtered and the solid product was washed with EtOH. The wet wt of the product was 21.62 g. The product was dried under vacuum to give 17.34 g (78%) of solid.

NMR data matched that of the mandelate salt of sertraline.

What is claimed is:

1. A process for preparing the optically pure (+) enantiomer of N-[4-(3,4dichlorophenyl)-3,4-dihydro-1(2H)-napthalenylidene]methaneamine, depicted below,

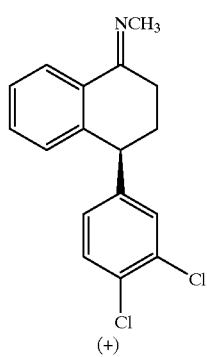

II (+)

or an optically enriched (+) mixture of the above compound of formula II and its opposite enantiomer, comprising reacting the optically pure (+) enantiomer of 4-(3,4-dichlorophenyl)-3,4dihydro-1(2H)-napthalenone ("the tetralone"), depicted below,

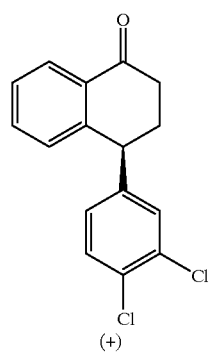

I (+)

or an optically enriched (+) mixture of the (+) and (−) enantiomers of the tetralone, with monomethylamine and either titanium tetrachloride or molecular sieves.

2. A process according to claim 1, wherein: (a) the ketimine product of formula II that is formed in such process is hydrogenated to form a mixture of cis (+) sertraline ("sertraline") and trans (−) sertraline; (b) sertraline is optionally separated from such mixture; and (c) sertraline is optionally converted into its hydrochloride or mandelate salt.

3. A process according to claim 1 wherein an excess of monomethylamine with respect to the tetralone starting material is employed.

4. A process according to claim 1 wherein the reaction is conducted at a temperature in the range of about −20° C. to about 60° C.

5. A process according to claim 1 wherein the solvent is selected from THF, methylene chloride, xylenes and dichlorobenzene.

6. A process according to claim 1 wherein monomethylamine and titanium chloride are reacted with the tetralone.

7. A process according to claim 1 wherein the tetralone is reacted with monomethylamine and molecular sieves.

8. A process according to claim 1 wherein the ketimine product of formula II or an optically enriched (+) mixture of such compound and its opposite enantiomer, is hydrogenated in situ in the same solvent in which it was formed to yield an optically pure mixture consisting of cis (+) sertraline and trans (−) sertraline, or a mixture consisting of cis (+) sertraline, cis (−) sertraline, cis (−) sertraline and trans (−) sertraline.

9. A process for preparing a mixture of cis (+) sertraline and trans (−) sertraline, comprising reacting the optically pure (+) enantiomer of 4-(3,4-dichlorophenyl)-3,4-dihydro-1(2H)-napthalenone ("the tetralone"), depicted below,

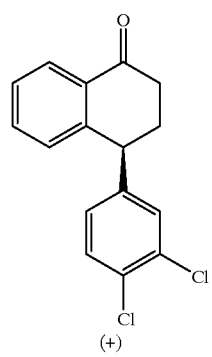

I (+)

or an optically enriched (+) mixture of the (+) and (−) enantiomers of the tetralone, with monomethylamine and either titanium tetrachloride or molecular sieves and a suitable hydrogenation catalyst in a suitable organic solvent under a hydrogen atmosphere at a pressure from about 20 psig to about 100 psig and a temperature from about room temperature to about 70° C.

* * * * *